United States Patent
Arnoldner et al.

(10) Patent No.: US 7,979,135 B2
(45) Date of Patent: Jul. 12, 2011

(54) COCHLEAR IMPLANT PITCH INTENSITY

(75) Inventors: Christoph Arnoldner, Vienna (AT); Jafar Sasan Hamzavi, Vienna (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 433 days.

(21) Appl. No.: 12/167,297

(22) Filed: Jul. 3, 2008

(65) Prior Publication Data
US 2009/0012580 A1 Jan. 8, 2009

Related U.S. Application Data

(60) Provisional application No. 60/947,727, filed on Jul. 3, 2007.

(51) Int. Cl.
*A61N 1/18* (2006.01)
(52) U.S. Cl. .......................... 607/55; 607/56
(58) Field of Classification Search ............... 607/54–57
See application file for complete search history.

(56) References Cited

U.S. PATENT DOCUMENTS

| | | | |
|---|---|---|---|
| 7,242,985 B1 * | 7/2007 | Fridman et al. | 607/56 |
| 7,251,530 B1 * | 7/2007 | Overstreet et al. | 607/55 |
| 7,493,170 B1 * | 2/2009 | Segel et al. | 607/57 |
| 7,702,396 B2 | 4/2010 | Litvak et al. | 607/57 |
| 2004/0015210 A1 * | 1/2004 | Clark et al. | 607/57 |
| 2004/0172101 A1 * | 9/2004 | Van Hoesel | 607/57 |
| 2004/0236390 A1 * | 11/2004 | Dadd et al. | 607/55 |
| 2005/0107843 A1 * | 5/2005 | McDermott et al. | 607/57 |

* cited by examiner

*Primary Examiner* — Carl H Layno
*Assistant Examiner* — Paula J Stice
(74) *Attorney, Agent, or Firm* — Sunstein Kann Murphy & Timber LLP

(57) ABSTRACT

A system and method are described for generating electrode stimulation signals for an implanted electrode array having multiple stimulation electrodes. An acoustic audio signal is processed to determine associated pitch characteristics and frequency component information. From the pitch characteristics and the frequency component information, electrode stimulation signals are determined which have intensity levels that reflect the pitch characteristics. Then audio nerve tissue is stimulated by applying the electrode stimulation signals to the electrodes in the implanted electrode array.

33 Claims, 11 Drawing Sheets

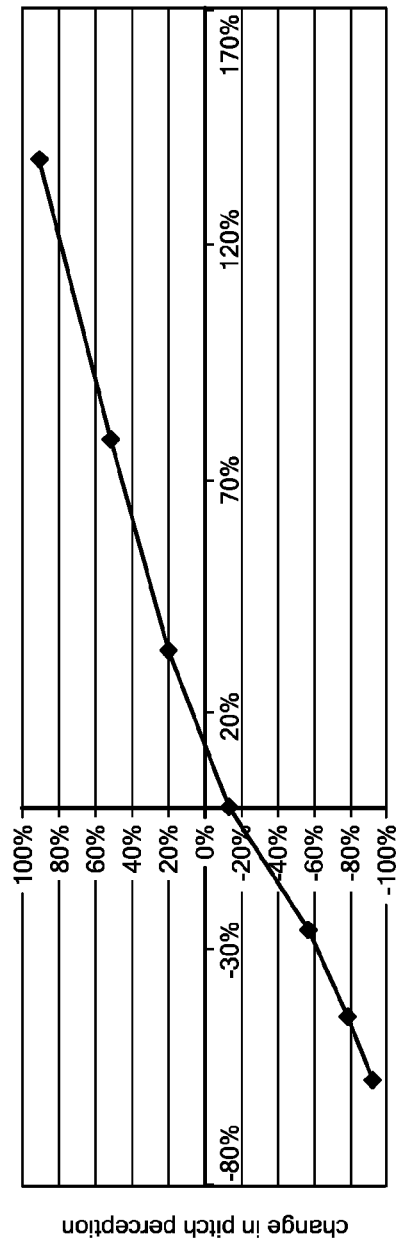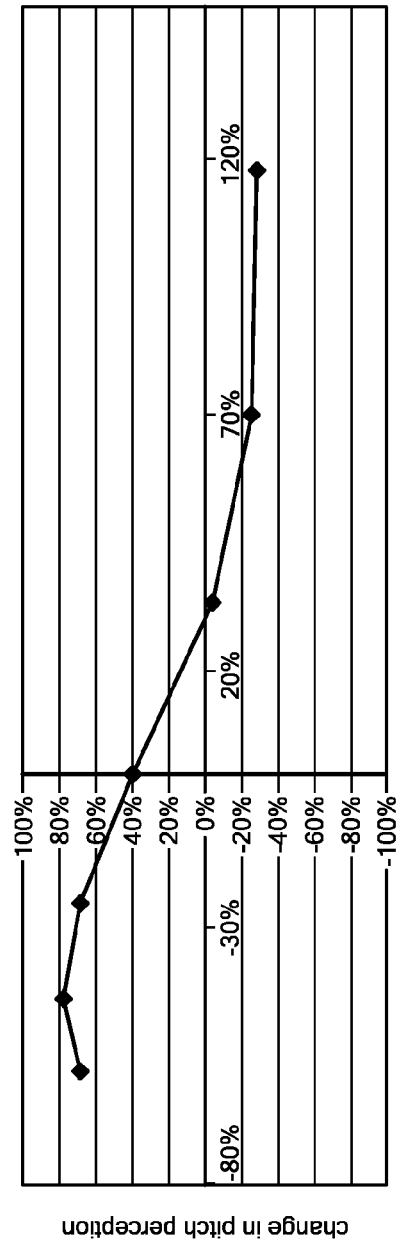
FIG. 5E
FIG. 5F

COCHLEAR IMPLANT PITCH INTENSITY

This application claims priority from U.S. Provisional Patent Application 60/947,727, filed Jul. 3, 2007, which is incorporated herein by reference.

FIELD OF THE INVENTION

The present invention relates to audio prostheses, and specifically to the signal processing used therein.

BACKGROUND ART

FIG. 1 shows a section view of an ear with a typical cochlear implant system. A normal ear transmits sounds through the outer ear 101 to the eardrum 102, which moves the bones of the middle ear 103, which in turn excites the cochlea 104. The cochlea 104 includes an upper channel scala vestibuli 105 and a lower channel scala tympani 106 which are connected by the cochlear duct 107. In response to received sounds transmitted by the middle ear 103, the fluid-filled scala vestibuli 105 and scala tympani 106 transmit fluid waves, functioning as an acoustic transducer to generate electric pulses that are transmitted to the cochlear nerve 108, and ultimately to the brain.

To overcome sensorineural hearing loss, a cochlear implant system produces direct electrical stimulation of the cochlea 104. This requires delivery of electrical power from outside the body through the skin to the implanted portion of the system, for example, by inductive coupling through the skin to transfer both the required electrical power and processed audio information for generating the electrical stimulation signals. In FIG. 1, an external transmitter coil 110 is coupled to an external signal processor and placed adjacent to a subcutaneous receiving coil 111 which is coupled to an implanted receiver processor 109. This arrangement inductively couples an audio information-bearing radio frequency (rf) electrical signal to the receiver processor 109. The receiver processor 109 is able to extract from the rf signal both a power component and the audio information.

In addition to extracting the audio information, the receiver processor 109 may also perform additional signal processing such as error correction, pulse formation, etc., and then produces a stimulation pattern based on the extracted audio information that is sent through connecting leads 112 to an implanted electrode carrier 113. Typically, this electrode carrier 113 includes multiple electrodes on its surface that provide selective electrical stimulation of the cochlea 104.

Various signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing.

For example, in the CIS approach, signal processing for the speech processor involves the following steps:
  (1) splitting up of the audio frequency range into spectral bands by means of a filter bank,
  (2) envelope detection of each filter output signal, and
  (3) instantaneous nonlinear compression of the envelope signal (map law).

Based on the tonotopic organization of the cochlea, each stimulation electrode in the scala tympani is associated with a band pass filter of the external filter bank and symmetrical biphasic current pulses are applied for stimulation. The amplitudes of the stimulation pulses are directly obtained from the compressed envelope signals. These signals are sampled sequentially, and the stimulation pulses are applied in a non-overlapping sequence. Thus, as a typical CIS-feature, only one stimulation channel is active at one time and the overall stimulation rate is comparatively high. For example, assuming an overall stimulation rate of 18 kpps and a 12-channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency.

Multichannel cochlear implants not only offer an opportunity to restore some degree of hearing to the profoundly deaf, but also can enable hearing sensations that mimic, at least to some extent, the attributes of normal acoustic hearing. Speech perception results have far exceeded the expectations of early investigators in the field. Taking into consideration that average monosyllabic word scores will reach nearly 80% in the next few years, current research efforts focus on the preservation of residual hearing and on a more natural sound sensation, especially for speech perception in noise and music perception.

Pitch plays a key role in the perception of speech and music, the recognition of a speaker's voice, and in analyzing complex auditory patterns. The two basic cues for pitch perception are the excitation position along the cochlea (place code—see Békésy GV, *Experiments In Hearing*, New York: McGraw Hill, 1960, incorporated herein by reference) and the temporal patterns of neural excitation (periodicity code—see Wever E., *Theory Of Hearing*, New York: Wiley, 1949, incorporated herein by reference). It is believed that both the temporal information and the correct tonotopic representation are necessary for complex pitch perception. In electrical stimulation, the perceived pitch depends on rate, level, waveform, and the place of stimulation, namely the position of the electrode. See Townshend B, Cotter N, Van Compernolle D, et al., *Pitch Perception By Cochlear Implant Subjects*, J. Acoust. Soc. Am. 1987; 82:106-115, incorporated herein by reference.

SUMMARY OF THE INVENTION

Embodiments of the present invention include a system and method for generating electrode stimulation signals for an implanted electrode array having multiple stimulation electrodes. An acoustic audio signal is processed to determine associated pitch characteristics and frequency component information. From the pitch characteristics and the frequency component information, electrode stimulation signals are determined which have intensity levels that reflect the pitch characteristics. The audio nerve tissue is then stimulated by applying the electrode stimulation signals to the electrodes in the implanted electrode array.

Further specific embodiments may also develop feedback information resulting from the stimulation of the audio nerve tissue. For example, the feedback information may include subjective feedback information from an implanted patient and/or objective feedback information from an implanted device. Then, the feedback information may be used to adjusting the system to customize the fit of the implanted electrode array for an implanted patient.

The electrode array may be a cochlear implant array such as a deep insertion array, or a brainstem array. The electrode stimulation signals may be monopolar stimulation signals.

DETAILED DESCRIPTION OF SPECIFIC EMBODIMENTS

Most pitch perception studies to date have focused on the influence of position and rate based mainly on relatively short electrode arrays using bipolar stimulation. See Collins L M, Zwolan T A, Wakefield G H, *Comparison Of Electrode Discrimination, Pitch Ranking, And Pitch Scaling Data In Postlingually Deafened Adult Cochlear Implant Subjects*, J. Acoust. Soc. Am. 1997; 101:440-455, which is incorporated herein by reference. But little attention has been given to the sensation of pitch in deeply inserted electrodes or the influence of stimulation intensity level on pitch perception. See Cohen L T, Busby P A, Whitford L A, et al., *Cochlear Implant Place Psychophysics—Pitch Estimation With Deeply Inserted Electrodes*, Audiol. Neurootol. 1996; 1:265-277, which is incorporated herein by reference.

This is rather surprising since the effect of acoustic stimulus intensity on perceived pitch was first reported over seven decades ago. See, Stevens S S, *The Relation Of Pitch To Intensity*, J. Acoust. Soc. Am. 1935; 6:150-154, which is incorporated herein by reference. Rhode discovered an intensity-dependent shift of the vibration peak of basilar membrane transfer functions (see Rhode W S, *Observations Of The Vibration Of The Basilar Membrane In Squirrel Monkeys Using The Mossbauer Technique*, J. Acoust. Sac. Am. 1971; 49 (Suppl. 2):1218-1230, which is incorporated herein by reference), and Zwislocki became the first to investigate these findings directly from the outer hair cells of Mongolian gerbils (see Zwislocki J J., *What Is The Cochlear Place Code For Pitch?* Acta. Otolaryngol. 1991; 111:256-262, which is incorporated herein by reference). As later confirmed for inner hair cells, this basal shift in the peak of cochlear excitation patterns after an increase in the sound pressure level (SPL) of the stimulating tone questioned the well-established place code for pitch. Up until then, this spatial code was thought to depend only insignificantly on sound intensity. It is clear that these shifts with acoustic stimulation, which might be caused by the mechanics of the basilar membrane, follow completely different rules than with electrical stimulation. In the latter, asymmetries in current spread might be responsible for its occurrence.

Figure 1:
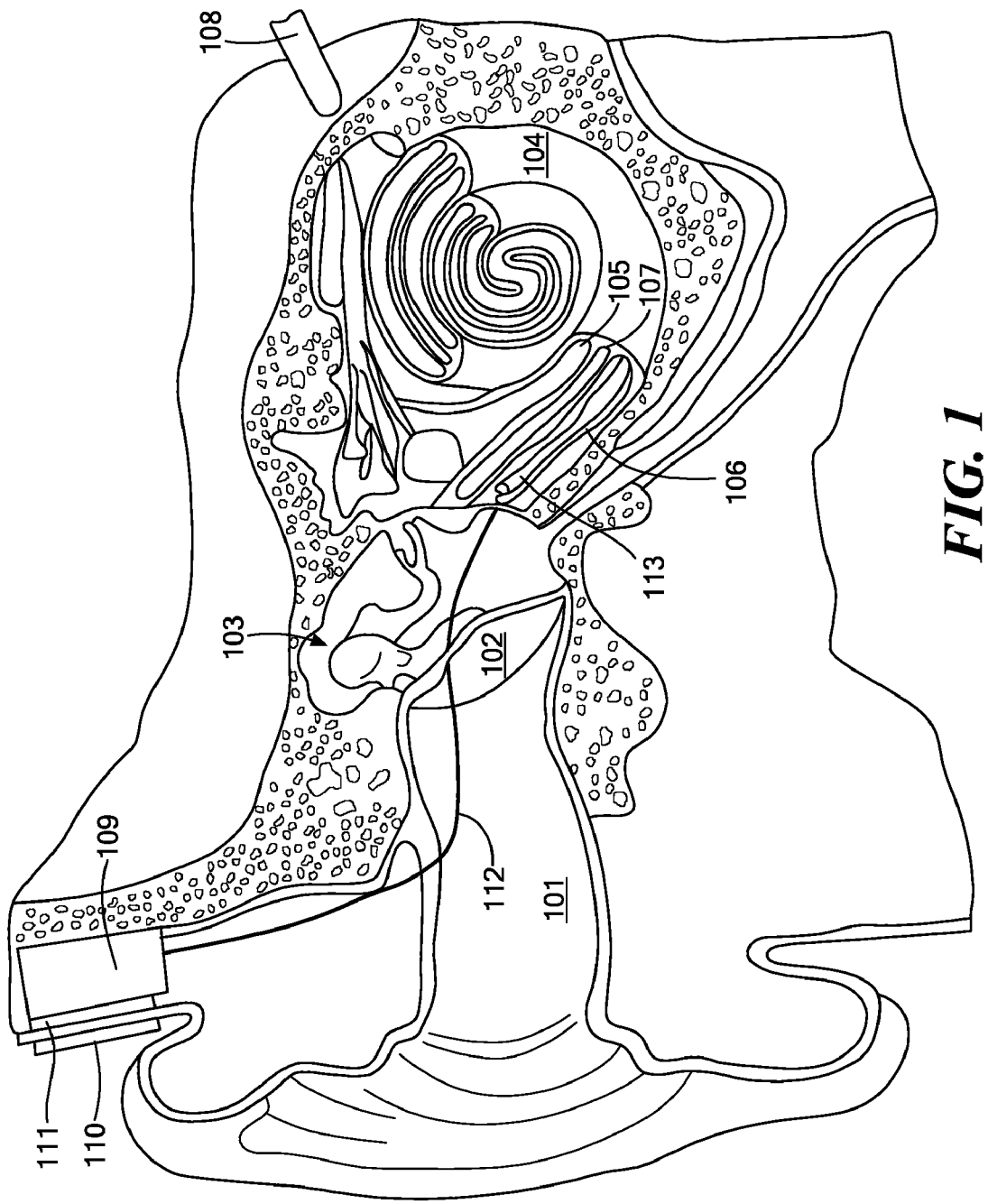
FIG. 1 shows a section view of an ear connected to a typical cochlear implant system according to an embodiment of the present invention.
Figure 2:
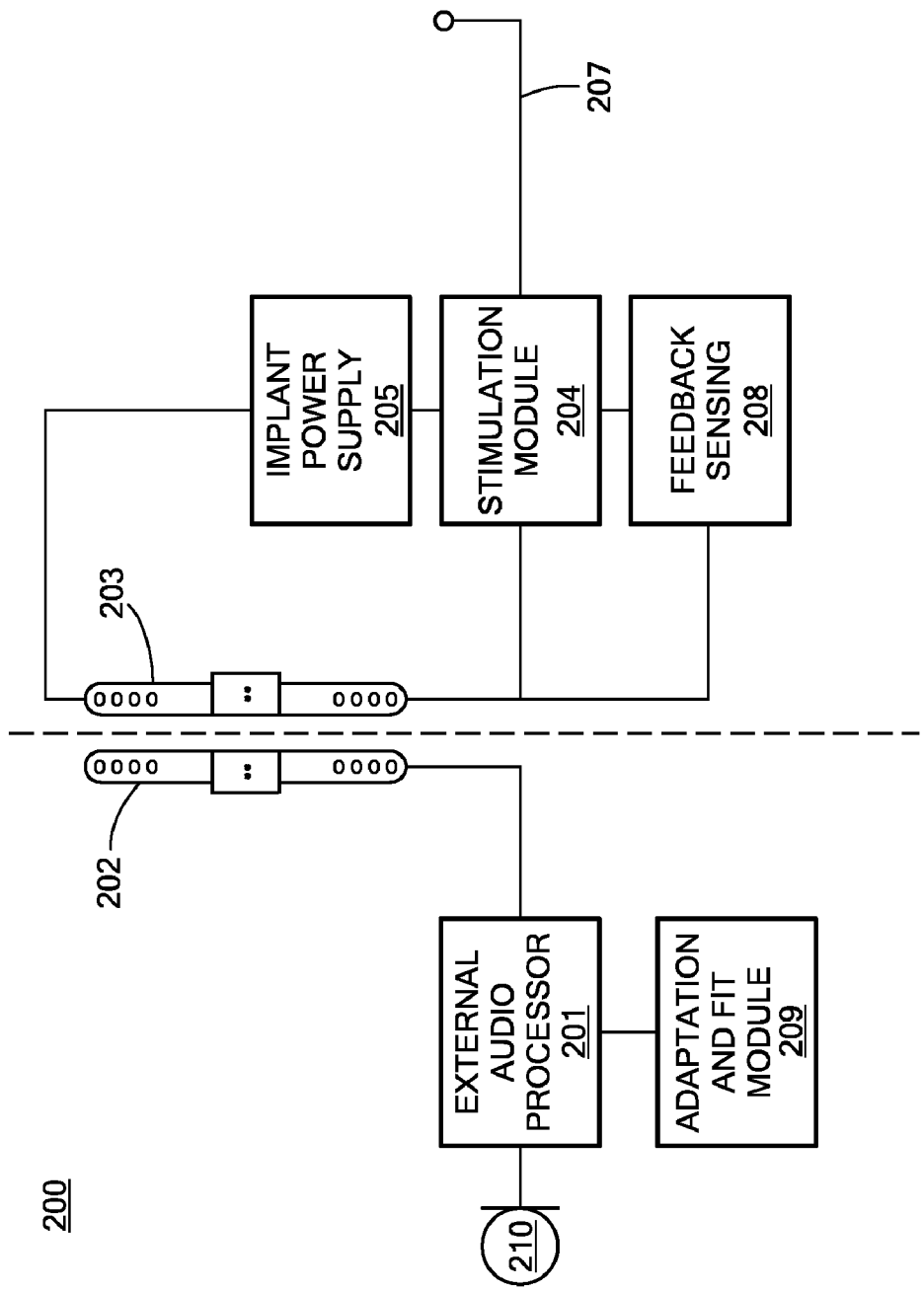
FIG. 2 shows various functional blocks in one embodiment of the present invention.
Figure 3:
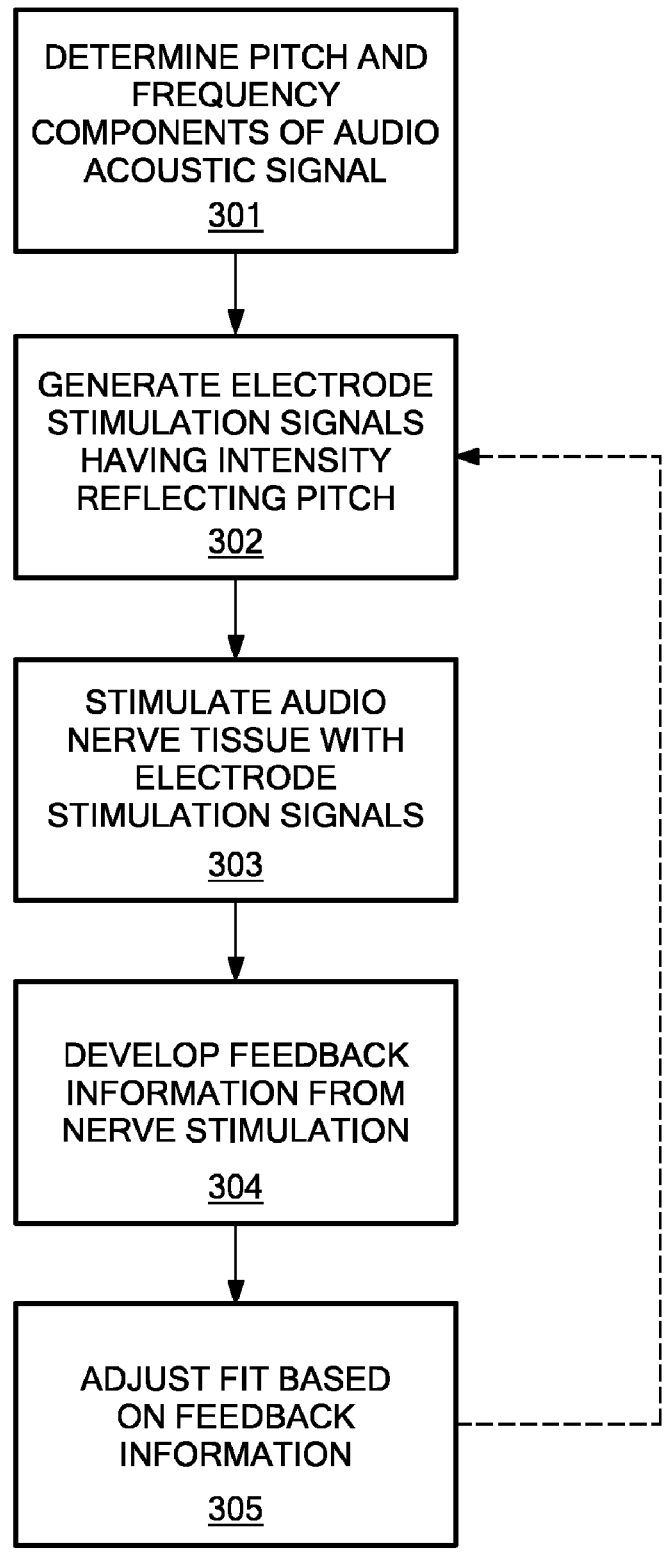
FIG. 3 shows various functional steps in a method according to one embodiment of the present invention.

Embodiments of the present invention are based upon using a relationship between stimulus intensity and pitch perception in audio prosthetic systems such as cochlear implants or brainstem implants. FIG. 2 shows various functional blocks in one embodiment of a system according to the present invention, while FIG. 3 shows various logical processing steps in a method according to the present invention. An external microphone 210 senses an acoustic audio signal representing sounds near to a patient user. The acoustic audio signal is processed by an external audio processor 201 to determine associated pitch characteristics and frequency component information, step 301. The processed audio acoustic signal is then coupled by external coil 202 transcutaneously to internal coil 203 (which also couple a power signal component to an implant power supply 205) for implanted stimulation module 204. From the pitch characteristics and the frequency component information determined by the audio processor 201, the stimulation module 204 generates electrode stimulation signals which have intensity levels that reflect the pitch characteristics, step 302. The stimulation module 204 may also perform additional signal processing such as error correction, pulse formation, etc. The electrode stimulation signals are then provided by the stimulation module 204 to the electrodes in the implanted electrode array 207, for example, by monopolar stimulation, to stimulate audio nerve tissue which the patient user perceives as sound, step 303.

As an alternative to the arrangement shown in FIG. 2, in other specific embodiments, the audio processor 201 might be implanted in the same housing as the stimulation module 204 so that all the audio signal processing is performed within the same physical element. Or in other embodiments, the audio processor 201 may be an external system element as shown in FIG. 2 and also include much of the functionality of the stimulation module 204 in selecting and forming the electrode stimulation signals, including developing the stimulation intensity as a function of the pitch characteristics, so that the implanted portion of the system need only develop the externally generated electrode stimulation signals for the electrode array 207, which may be a cochlear implant array such as a deep insertion array, or a brainstem array.

Further specific embodiments may also develop feedback information resulting from the stimulation of the audio nerve tissue, step 304. For example, the feedback information may include subjective feedback information from an implanted patient and/or objective feedback information from an implanted device. The system shown in FIG. 2 includes an implanted feedback sensing module 208 which senses objective operating characteristics of the implant system. The sensed feedback information is passed back from the implanted coil 203 to the external coil 202 and back to adaptation and fit module 209 where it may be used to adjusting the system to customize the fit of the implanted electrode array for an implanted patient, step 305. For example, depending on the sensed feedback information and/or subjective responses from the patient user, the stimulus intensity of individual frequency channels and/or stimulation electrodes may adjusted to optimize pitch perception.

During the fitting procedure, step 305, the existence, extent, and quality of the intensity-pitch effect is evaluated (among other things). The most basal and the most apical channel can be stimulated to define the range of perceptible pitch changes and a reference tone with a comfortable intensity can be defined. Then test tones with changing intensity within the dynamic range of a medio-cochlear channel can be stimulated. The subject is requested to quantify the pitch of the test tone in comparison to the reference tone with constant level. Results can be depicted on a diagram which is integrated in the fitting software. In this way the quality (higher or lower pitches with changing intensity) and quantity (compared to the pitch range defined in the beginning of the procedure) of the intensity-pitch effect can be evaluated. Through a mathematical algorithm the measured pitch shifts are compensated according to its parameters. Such techniques may enhance music perception in that, even with changing intensity, a more balanced and therefore more physiological sound percept is reached.

Experimental Tests. As reported in Arnoldner et al., *The Role of Intensity Upon Pitch Perception in Cochlear Implant Recipients*, in Laryngoscope, 116(10): 1760-1765, October 2006, which is incorporated herein by reference, thirteen post-lingually deafened Med-El (Innsbruck, Austria) Combi 40 (C40) or Combi 40+(C40+) cochlear implant patients participated in an experimental study based on an 8-(C40) or 12-channel (C40+) implant using a monopolar stimulation mode with a maximum pulse repetition rate up to 18,180 pulses per second (pps). The standard electrode measured 31.5 mm with contacts distributed equally over 26.4 mm (C 40: 19.6 mm) and with an electrode spacing of 2.4 mm (C 40: 2.8 mm). Demographic details of the subjects are given in Table I:

electrode (5 single instead of paired contacts at the tip), and in two patients, a shorter version of the Med-El electrode ("m" electrode) was used. At follow-up, all patients demonstrated open set speech recognition, with an average score for monosyllables of 56% correct (range 30-82%), 91% for the number test (range 73-100%), and 86% (range 45-99%) for the Innsbrucker sentence test.

Psychophysical Procedures—Pitch estimation along electrode array. To demonstrate the integrity of the electrodes, standard telemetry (impedance) testing was used. Because loudness affects the perceived pitch, a loudness balance for all channels was exercised: one stimulus was chosen as a reference tone with a comfortable level. Then, in a direction from apical to basal, a paired comparison of two electrodes was performed. With use of a visual scale, the subject adjusted each stimulus to comfortable levels in an ascending-descending technique. To recheck equal loudness of all electrodes, stimuli were presented sequentially again, and necessary adjustments were made. With use of biphasic bursts of 50 ms duration, the most basal and most apical channel was presented to the subject as reference tones. On a visual analogue scale ranging from 0 (lowest pitch) to 120 (highest pitch), the reference tones were defined as 20 for the most apical electrode and 80 for the most basal electrode. All active channels were presented in a randomized order with three repetitions of each channel. The subject was asked to quantify the perceived pitch on the scale. No feedback was provided. Before

TABLE I

Demographic Data of All Patients.

| Patient Number | Sex | Etiology | Age at Implant (yr) | CI Experience (yr) | Implant | Electrode | Insertion Depth (mm) | Percent Correct (monosyllable/ number/sentences) |
|---|---|---|---|---|---|---|---|---|
| 1 | M | Progressive | 57.9 | 3.25 | C 40+ | Standard | 33 | 58/93/99 |
| 2 | M | Ménière, otosclerosis | 63.2 | 2.8 | C 40+ | Standard | 30 | 68/93/94 |
| 3 | M | Skull trauma | 44.47 | 9.35 | C 40 | Standard | 30 | 78/98/99 |
| 4 | M | Progressive | 61.06 | 5.02 | C 40+ | Standard | 30 | 72/100/98 |
| 5 | M | Progressive | 36.36 | 10.2 | C 40 | Standard | 25 | 82/100/99 |
| 6 | M | RWM rupture | 64.41 | 2.56 | C 40+ | Standard | 30 | 30/80/72 |
| 7 | F | Progressive | 50.12 | 2.09 | C 40+ | Standard | 30 | 47/78/99 |
| 8 | M | Progressive | 46.90 | 1 | C 40+ | Flex soft | 31 | 49/95/DNT |
| 9 | M | Progressive | 54.27 | 2.4 | C 40+ | Standard | 30 | 35/75/45 |
| 10 | F | Progressive | 64.75 | 8.82 | C 40 | Standard | 30 | 77/100/99 |
| 11 | F | Progressive | 59.23 | 3.84 | C 40+ | Standard | 20 | 35/73/53 |
| 12 | F | Progressive | 60.02 | 1.23 | C 40+ | m-electrode | 21 | 52/95/DNT |
| 13 | F | Progressive | 65.2 | 1.15 | C 40+ | m-electrode | 21 | 40/100/DNT |
| Mean | 5 F/8 M | | 55.99 | 4.13 | | | 28 | 56/91/86 |

RWM = round window membrane;
DNT = did not test.

In ten of the patients, a standard Med-El deep insertion electrode was inserted on average 30 mm into the cochlea. For all subjects, the insertion depth was estimated by the surgeon at the time of insertion, and the electrode's postoperative position and depth of insertion was radiologically assessed using conventional radiographs and a modified Chausse III projection. One patient was supplied with the "flex soft"

data collection, all patients received 1 hour of pitch ranking practice using a training program on a personal computer.

Pitch estimation with varying intensity of test stimulus. In this procedure, the most apical, the most basal, and two to three channels in between were stimulated in consecutive order as shown in Table II:

TABLE II

Partial Spearman Correlation Coefficeints and Testing Parameters for All Patients.

| Correlation | Patient Number | Partial Correlation Coefficients | Channels Tested | Mean Dynamic Range (cu) | Stimulation Rate (pulse/s) | Pulse Duration (µs) |
|---|---|---|---|---|---|---|
| Very strong positive | 5 | 0.99395 | 1, 4, 7 | 257-1,352 | 1,714 | 40 |
| | 12 | 0.96910 | 1, 4, 7, 9, 11 | 103-570 | 1,515 | 26.67 |
| | 10 | 0.96058 | 1, 4, 8 | 313-732 | 1,500 | 40 |

TABLE II-continued

Partial Spearman Correlation Coefficeints and Testing Parameters for All Patients.

| Correlation | Patient Number | Partial Correlation Coefficients | Channels Tested | Mean Dynamic Range (cu) | Stimulation Rate (pulse/s) | Pulse Duration (µs) |
|---|---|---|---|---|---|---|
| | 4 | 0.95137 | 1, 4, 7, 9, 12 | 293-1,097 | 1,515 | 26.67 |
| | 7 | 0.93715 | 1, 4, 7, 9, 12 | 133-524 | 1,515 | 26.67 |
| | 11 | 0.92746 | 1, 4, 7, 12 | 204-387 | 1,515 | 26.67 |
| | 1 | 0.90180 | 1, 7, 9 | 253-1,080 | 1,644 | 26.67 28.33 (7) |
| Strong positive | 3 | 0.77948 | 1, 4, 8 | 295-1,489 | 1,500 | 40 |
| | 8 | 0.73085 | 2, 5, 8, 11 | 181-686 | 1,714 | 26.67 |
| | 9 | 0.70737 | 1, 7, 10 | 180-392 | 1,515 | 26.67 |
| Negative | 13 | −0.48091 | 1, 4, 7, 9 | 279-572 | 2,020 | 26.67 |
| | 2 | −0.49235 | 4, 6, 9 | 250-780 | 1,744 | 26.67 35 (6) |
| | 6 | −0.92125 | 2, 8, 11 | 286-1,330 | 1,527 | 26.67 |

If the pulse amplitude changed in a channel-dependent manner, the respective channel is in parentheses.

After testing the threshold and the maximum acceptable loudness level, a 50 ms biphasic stimulus at comfortable loudness level was presented to the subject as a fixed reference tone. This tone's pitch was defined as 0% on a visual analogue scale ranging from −100% (lowest pitch) to 100% (highest pitch). Subsequently, a second tone was played with varying intensity: between two and three steps in intensity up and down from the reference tone within the dynamic range were defined. The amplitude of the intensity steps depended on the dynamic range of the channel and differed from 21 to 499 cu (mean 115 cu). If a channel's dynamic range was too small to perform at least four significant intensity changes, an adjacent channel (more apical or more basal) was used. All levels of intensity were presented four times in random order. The subject was asked to quantify the pitch of the test tone in comparison with the reference using the visual scale. Each subject was strictly instructed to ignore the volume and to focus on the perceived pitch of the tone. To rule out any confusion between the perception of loudness and the perception of pitch, subjects were asked to judge both qualities (e.g., "louder and higher") simultaneously. No feedback was provided. For each stimulated channel, the results of the four repeated quantifications at the same level of intensity were combined to a mean value. Only these mean values were then used for statistical analyses.

Statistical Methods. To describe the dependence of pitch perception on the varying intensity of the stimulus, the Spearman correlation coefficient was calculated for every subject at each tested channel. The partial Spearman correlation coefficient was calculated for every subject to obtain a channel-adjusted measure of correlation. Unlike the ordinary correlation coefficient, the partial correlation coefficient can be compared between patients that were stimulated at different channels. The percentage of patients with a positive partial correlation and the corresponding 95% confidence interval (CI) was calculated. To test for a systematic influence of the channel on the degree of correlation, a linear mixed model was used, including the following factors: the subject as a random factor and the channel number (1=the most apical channel; 12=the most basal channel) as a continuous covariate.

Laboratory Equipment. The stimuli were generated on a personal computer using the Med-El standard Studio+clinical software. The electrodes were stimulated in monopolar mode. Maximum stimulation rates were between 1500 pps and 2020 pps per electrode, depending on the number of active channels as set forth in Table II.

Figure 4:
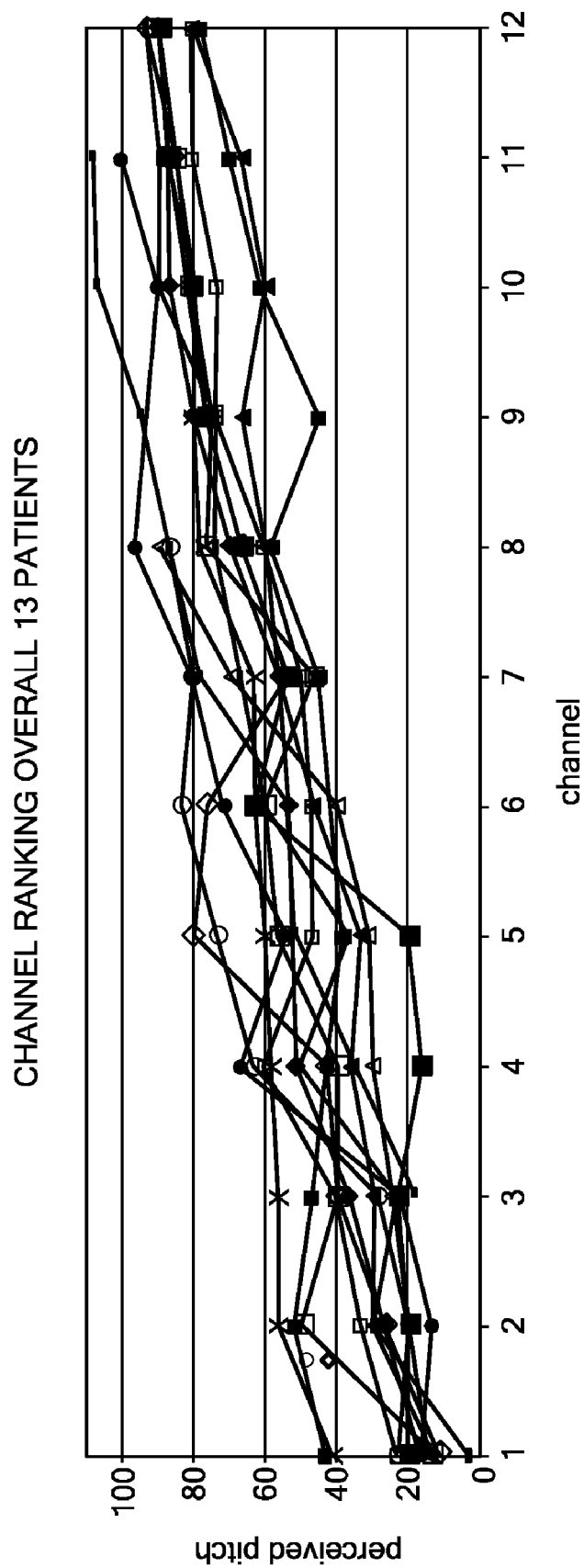
FIG. 4 shows a channel ranking for patients in one experiment in pitch perception according to the invention.
Figure 5A:
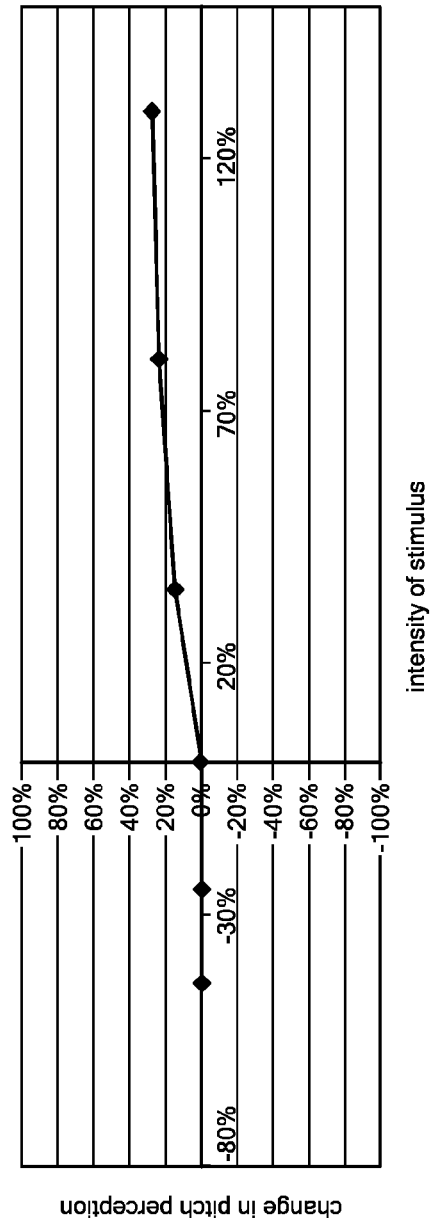
FIG. 5 shows perceived pitch as a function of stimulus intensity in one experiment according to the invention.
Figure 5B:
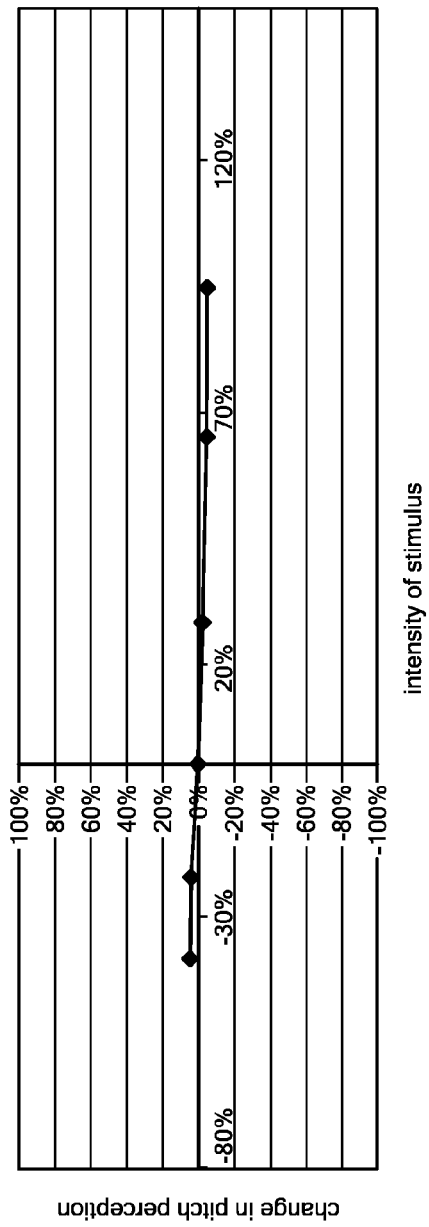
Figure 5C:
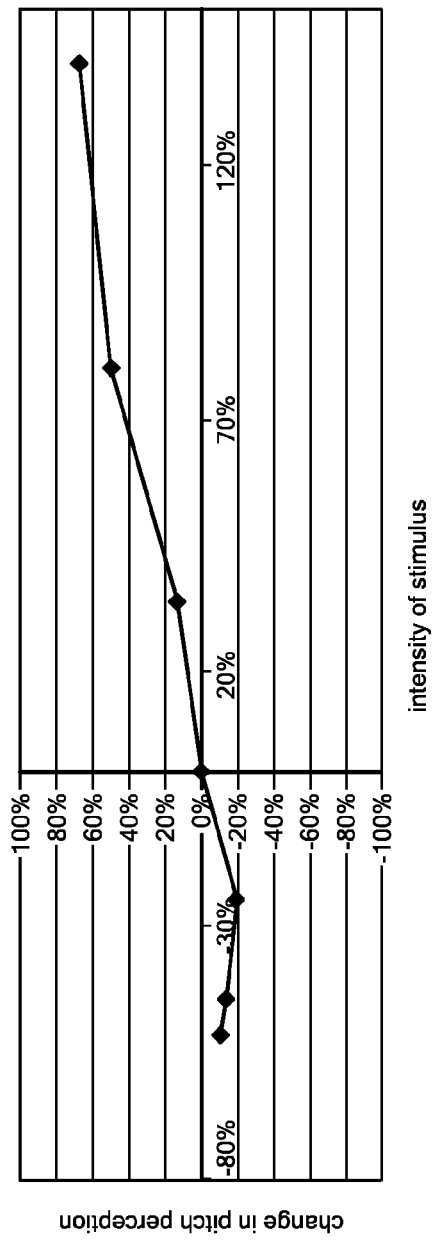
Figure 5D:
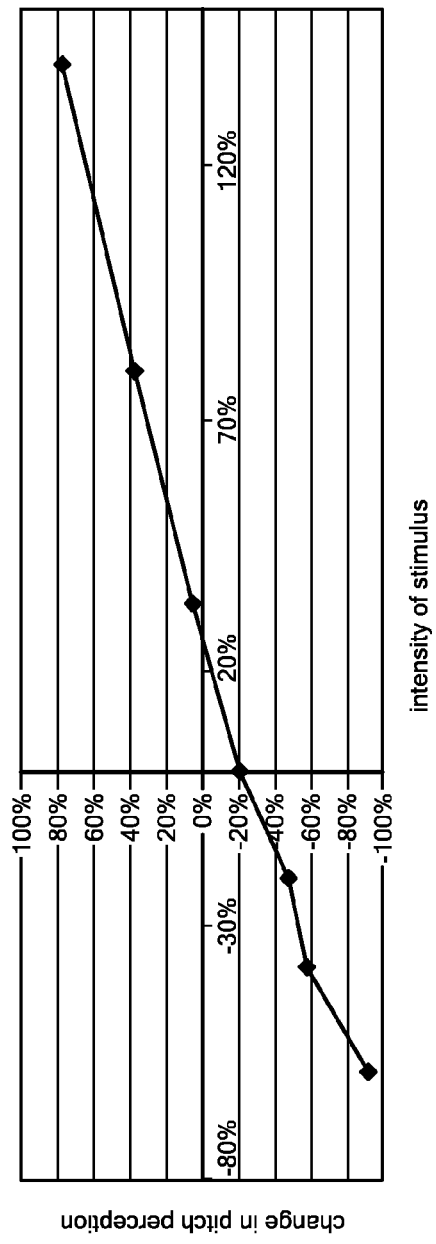
Figure 5G:
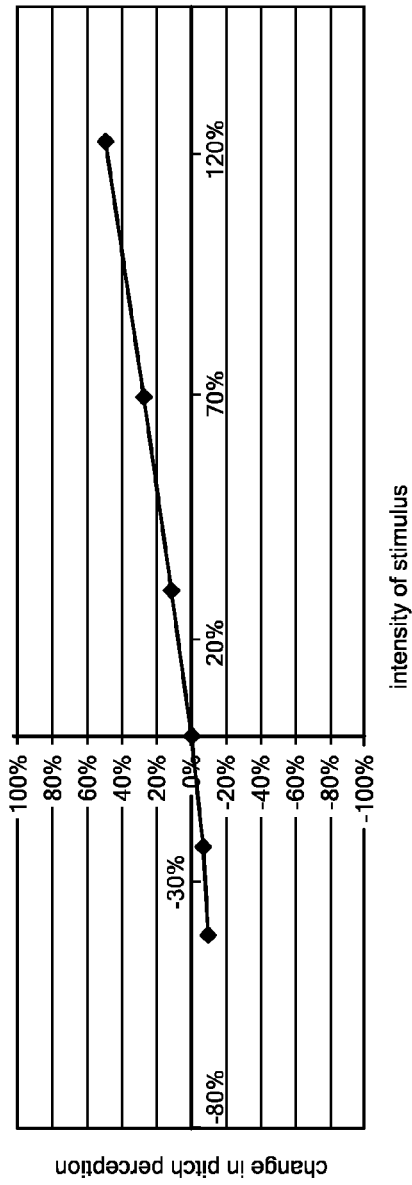
Figure 5H:
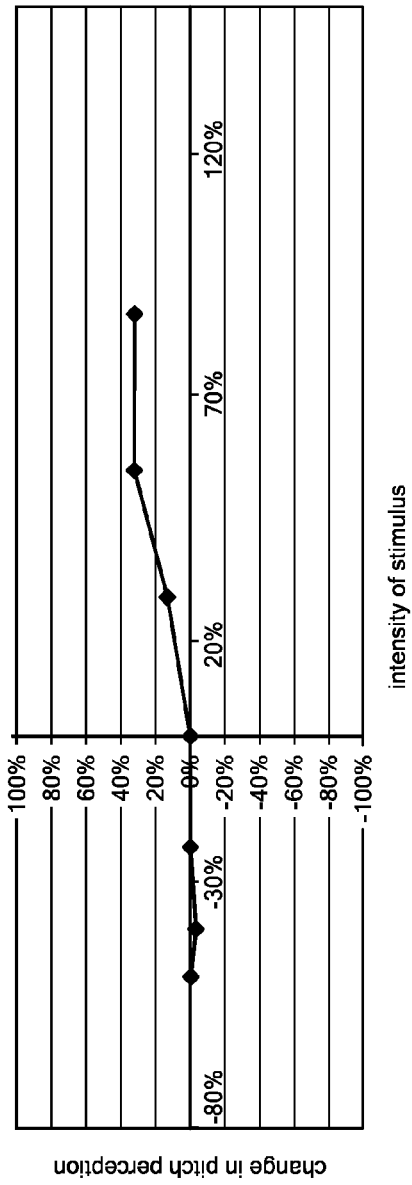
Figure 5I:
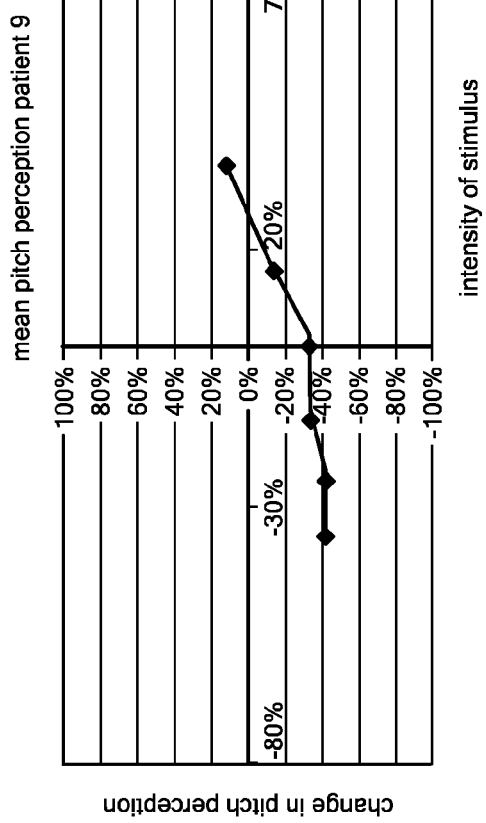
Figure 5J:
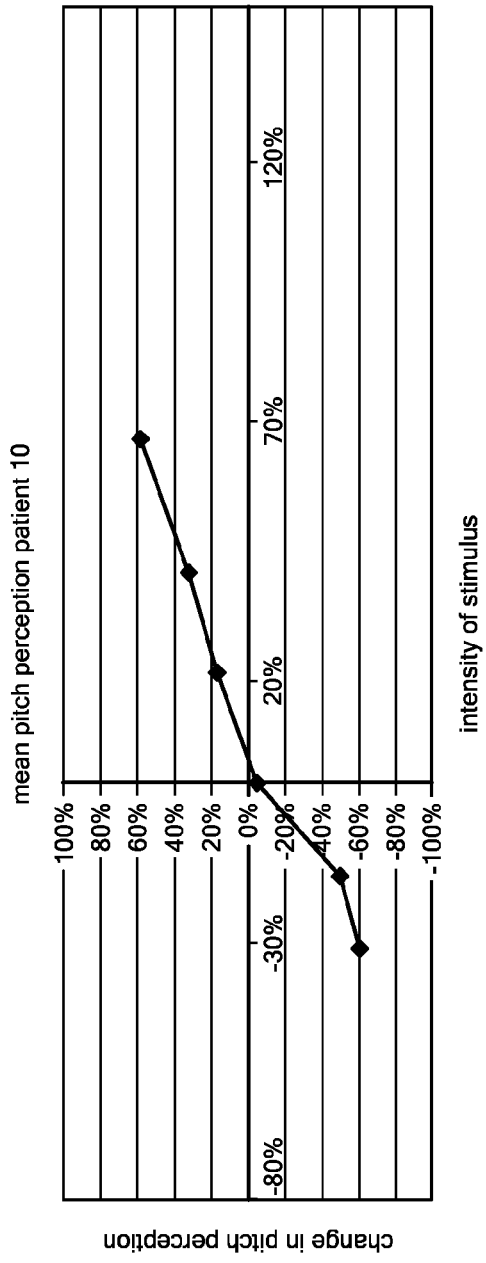
Figure 5K:
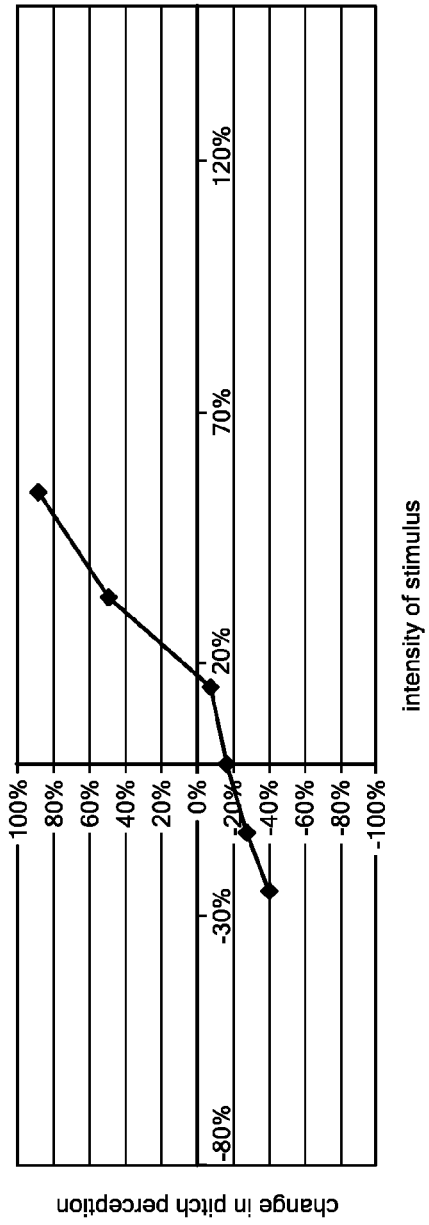
Figure 5L:
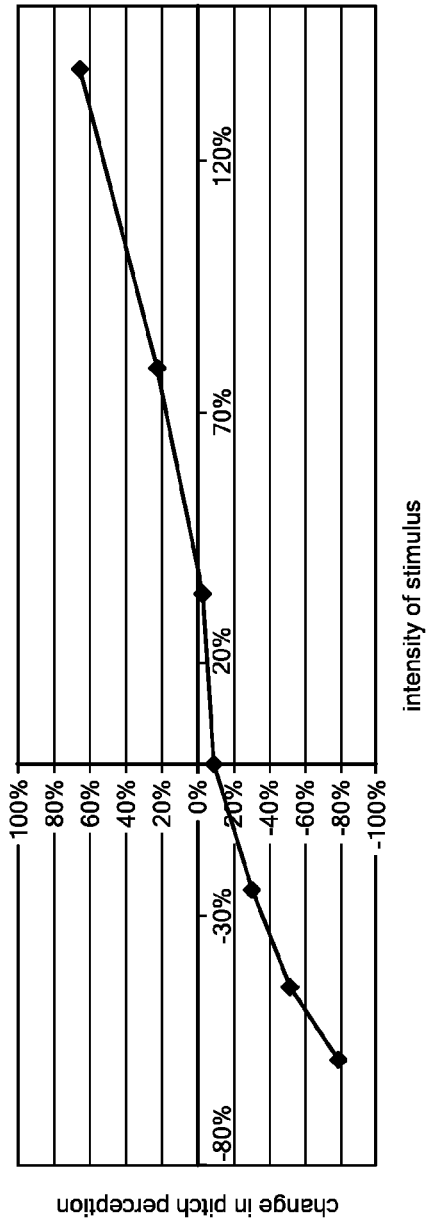
Figure 5M:
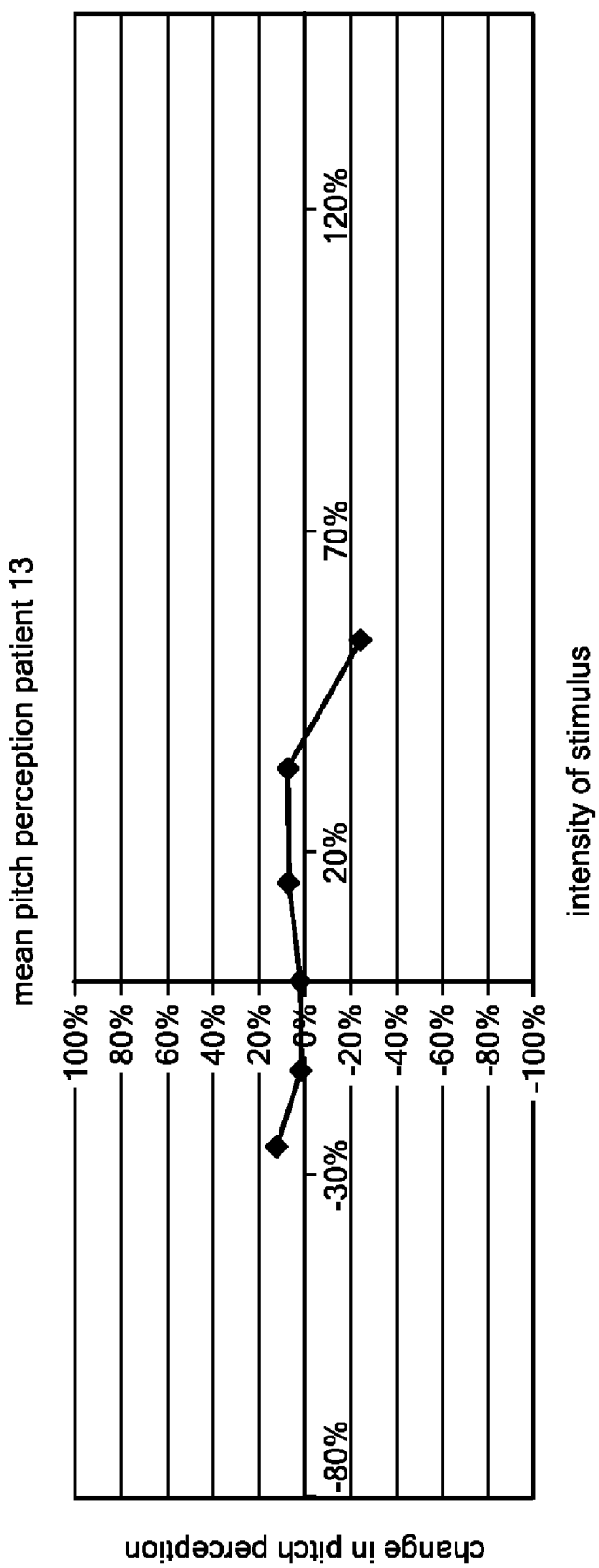

Results—Pitch Estimation along Electrode Array. All patients exhibited a clear place-pitch ability across the whole range of the electrode array as shown in FIG. 4 (from the Arnolder et al. Laryngoscope article). This means that pitch percept changed with place of stimulation. Thus, all patients were able to judge pitch with their cochlear implants, and the criteria for the second test were met.

Pitch Estimation with Varying Intensity of Test Stimulus. Eleven of the 13 patients tested were found to perceive a clear change in pitch with varying intensity of the stimulus as shown in FIG. 5 (from the Arnolder et al. *Laryngoscope* article) and Table II.

Ten of these patients reported an increase in pitch with increasing stimulus level (partial correlation coefficients ranging from 0.99-0.71), whereas one patient reported the opposite effect ($r=-0.92$). This patient perceived lower pitches with higher levels of stimulation of the test tone. Two subjects (subjects 2 and 13) perceived only minor pitch changes with varying intensity ($r=-0.49$ and $r=-0.48$, respectively). Therefore, 77% of the patients (95% CI: 54-100%) demonstrated a positive correlation. Generally, there was no evident difference in the correlation between apical, basal, or mediocochlear channels tested ($P=0.87$). Subjects 2 and 13 were the only patients who showed a channel-dependent relation of pitch on intensity: patient 2 had very strong negative correlations for channels 4 and 9 ($r=-0.96$ and $r=-0.97$) and a strong positive correlation for channel 6 ($r=0.79$). After averaging these results, there appears to exist no pitch-intensity dependence (FIG. 2). Patient 13 also showed strong negative correlations on two channels (4: $r=-0.95$; 7: $r=-0.7$) and a positive correlation on another channel (9: $r=0.56$). These patients had no peculiarities as far as implant experience, age at implantation, or postoperative performance are concerned.

This data represents one of the first descriptions of a distinct dependence between pitch perception and intensity in a total of 11 (of 13) cochlear implant recipients. This dependence was found to exist in people with normal hearing decades ago. In 1935, Stevens reported on three normal hearing subjects who experienced a decrease in pitch with increasing intensity for tones below 500 Hz and an increase in pitch with increasing intensity for tones above 3,000 Hz. Stevens S S, *The Relation Of Pitch To Intensity*, J. Acoust. Soc. Am. 1935; 6:150-154. He explained this phenomenon, named Steven's rule, as a peripheral mechanism caused by the resonant characteristics of the ear. The range of pitch change was rather modest, not exceeding approximately a 13% change in frequency. Cohen, also reported no significant pitch changes and hypothesized a subject-unique pitch-intensity relationship. Cohen A, *Further Investigation Of The Effects Of Intensity Upon The Pitch Of Pure Tones*, Acoust. Soc. Am. 1961; 33: 1363-7136, which is incorporated herein by reference. Verschuure and van Meeteren found the intensity steps used by Cohen to be too large and did find significant changes in pitch perception. Verschuure J, Van Meeteren A A, *The Effect Of Intensity On Pitch*, Acustica 1975; 32:33-44, which is incorporated herein by reference.

With the advent of cochlear implants, Zwislocki started to reinvestigate the cochlear code for pitch, especially the dependence between intensity and pitch. Zwislocki J J., *What Is The Cochlear Place Code For Pitch? Acta. Otolaryngol.* 1991; 111:256-262. In the receptor potentials recorded from Mongolian gerbil hair cells, he found that the excitation maximum moved toward the base of the cochlea when the sound intensity of an acoustical stimulus was increased. This shift was quantified as one to two octaves corresponding to 2 mm along the cochlear canal, when the SPL was increased from 20 to 80 dB in the mid-frequency range. This contrasted with Steven's rule, which described only small pitch changes with varying intensity. Therefore, the current place code of pitch, with the excitation maximum serving as the only adequate code for pitch perception, was questioned.

Whereas Steven's rule was demonstrated as valid for acoustical hearing in people with normal hearing, Zwislocki found the shift of excitation maxima in receptor potentials in animals. So far, pitch perception studies in cochlear implant recipients have paid only little attention to this phenomenon. In 1987, Townshend et al. investigated the effects of place, rate, and level of stimulus on pitch. Townshend B, Cotter N, Van Compernolle D, et al., *Pitch Perception By Cochlear Implant Subjects*, J. Acoust. Soc. Am. 1987; 82:106-115. The influence of stimulus level on pitch perception was described as negligible, necessitating no compensation, and place and rate were found to be key factors in the discrimination of pitch, despite the large variability among subjects. Also, Pijl found a large variability among the subjects tested using a pulse rate matching procedure: two patients of three showed a trend toward lower pitch percepts with increasing amplitude. Pijl S, *Pulse Rate Matching By Cochlear Implant Patients: Effects Of Loudness Randomization And Electrode Position*, Ear Hear 1997; 18:316-325, which is incorporated herein by reference. In contrast, we found rather uniform results: 11 of the 13 patients tested were found to show a clear pitch/intensity dependence. In 10 of those, pitch increased with increasing stimulus level. One patient (subject 6) exhibited the reverse effect, namely, pitch became markedly lower with increasing intensity of stimulus. Of note is the etiology of this patient's deafness, namely, rupture of the round window membrane. As far as the threshold levels are concerned, this patient's values were found to be rather high but still not outstanding (Table II). With the current standard of knowledge, we can only hypothesize the role these characteristics may play. The same holds true for subjects 2 and 13, the only patients who showed a channel-dependent relation of pitch on intensity.

The mechanism of the phenomenon of perceiving higher pitches with increasing intensity of stimulus, found in as many as 77% of our subjects, remains unclear because electrical hearing with implants follows completely different rules than acoustical hearing. In the latter, the same findings have been known for a long time, whereas for electrical hearing, studies on a higher number of subjects have been rather scarce, as mentioned above. Clearly, increasing the stimulation level increases the extent of the electrical field, therefore increasing the amount of neural tissue stimulated. However, the question remains as to why this enlargement of the electrical field leads rather uniformly to an increase in pitch. One could assume that both more basal and more apical neural structures would be stimulated equally, producing no effect at all. In fact, the changing diameter of the cochlear duct as well as the non-uniform density of the neural tissue appear to favor a path of the electrical field toward the cochlear base. In this sense, a larger electrical field leads to a stronger activation of the basal ganglion cells and therefore an increase in pitch sensation. The individual population of excitable neural tissue as well as the exact location of the electrode within the scala tympani certainly influences this effect in one direction or another.

However, in our subjects, we found nearly uniform results, with no difference between places of stimulation (same results for different channels tested). Another phenomenon with increasing current level is the so-called ectopic or cross-turn stimulation. See Frijns J H, Briaire J J, Grote J J, *The Importance Of Human Cochlear Anatomy For The Results Of Modiolus-Hugging Multichannel Cochlear Implants*, Otol. Neurotol. 2001; 22:340-349, which is incorporated herein by reference. This cross-turn stimulation occurs when auditory nerve fibers originating from more apical regions and running centrally in the modiolus are stimulated at higher stimulation levels. This counteracts the basal spread of the electrical field described above. The results in our patients show that both mechanisms appear to take place in a parallel fashion and that in most patients the downward shift appears to prevail over the cross-turn stimulation.

It is certainly true that it is difficult to independently judge the pitch of two tones that differ significantly in volume. Nevertheless, we do believe that the findings described are in fact reliable and reproducible: 1) in test number one, all patients demonstrated that they were indeed able to judge pitch at all; 2) subjects were repeatedly advised to focus on the pitch of the tones and to ignore the volume; 3) subjects were advised to judge both qualities (loudness and pitch) simultaneously to control its independent judgment.

Our data show that a distinct relation between intensity of stimulus and pitch perception exist in cochlear implant recipients using monopolar stimulation. Despite the preliminary nature and the high individual variability of the results, we suggest that the findings described need to be implemented in today's speech coding strategies. Even if normal auditory perception of speech works very well without any compensation, we believe that further improvements in the patient's performance (e.g., perception of music, speech in noise) could be achieved by compensating the intensity effect described herein. Future studies should be undertaken to achieve a method of quantification of the pitch-intensity effect, to explore the effect of different stimulation modes, and to test a greater number of subjects.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for an implanted electrode array having a plurality of electrodes, the method comprising:
   processing an acoustic audio signal to determine associated pitch characteristics and frequency component information;
   generating a set of electrode stimulation signals from the determined pitch characteristics and frequency component information, each generated electrode stimulation signal corresponding to a respective electrode of the plurality of electrodes, including increasing an intensity level of at least one of the electrode stimulation signals to cause a change in pitch perception; and stimulating audio nerve tissue by applying the set of electrode stimulation signals to the plurality of electrodes in the implanted electrode array.

2. A method according to claim 1, wherein the implanted electrode array is a cochlear implant array.

3. A method according to claim 2, wherein the cochlear implant array is a deep insertion array.

4. A method according to claim 1, wherein the implanted electrode array is a brainstem array.

5. A method according to claim 1, wherein the set of electrode stimulation signals is a set of monopolar stimulation signals.

6. A method according to claim 1, further comprising:
developing feedback information resulting from the stimulation of the audio nerve tissue.

7. A method according to claim 6, wherein the feedback information includes subjective feedback information from an implanted patient user.

8. A method according to claim 6, wherein the feedback information includes objective feedback information from an implanted device.

9. A method according to claim 6, further comprising:
adjusting the method based on the feedback information to customize fit of the implanted electrode array for an implanted patient user.

10. A method according to claim 1, wherein increasing the intensity level of the at least one of the electrode stimulation signals causes a perceived increase in pitch.

11. A method according to claim 1, wherein increasing the intensity level of the at least one of the electrode stimulation signals causes a perceived decrease in pitch.

12. An audio prosthetic system comprising:
an audio processor for processing an acoustic audio signal to determine associated pitch characteristics and frequency component information;
an implantable electrode array having a plurality of stimulation electrodes for stimulating audio nerve tissue with a set of electrode stimulation signals; and
a stimulation module for generating the set of electrode stimulation signals from the determined pitch characteristics and frequency component information, each generated electrode stimulation signal corresponding to a respective electrode of the plurality of stimulation electrodes, including increasing an intensity level of at least one of the electrode stimulation signals to cause a change in pitch perception.

13. An audio prosthetic system according to claim 12, wherein the implantable electrode array is a cochlear implant array.

14. An audio prosthetic system according to claim 13, wherein the cochlear implant array is a deep insertion array.

15. An audio prosthetic system according to claim 12, wherein the implantable electrode array is a brainstem array.

16. An audio prosthetic system according to claim 12, wherein the set of electrode stimulation signals is a set of monopolar stimulation signals.

17. An audio prosthetic system according to claim 12, further comprising:
a feedback sensing module for developing feedback information resulting from the stimulation of the audio nerve tissue.

18. An audio prosthetic system according to claim 17, wherein the feedback information includes subjective feedback information from an implanted patient user.

19. An audio prosthetic system according to claim 17, wherein the feedback information includes objective feedback information from an implanted device.

20. An audio prosthetic system according to claim 17, further comprising:
a user fit module for adjusting the system based on the feedback information to customize fit of the implantable electrode array for an implanted patient user.

21. An audio prosthetic system according to claim 12, wherein increasing the intensity level of the at least one of the electrode stimulation signals causes a perceived increase in pitch.

22. An audio prosthetic system according to claim 12, wherein increasing the intensity level of the at least one of the electrode stimulation signals causes a perceived decrease in pitch.

23. An audio prosthetic system comprising:
means for processing an acoustic audio signal to determine associated pitch characteristics and frequency component information;
means for stimulating audio nerve tissue by applying a set of electrode stimulation signals to a plurality of stimulation electrodes in an implantable electrode array; and
means for generating the set of electrode stimulation signals from the determined pitch characteristics and frequency component information, including increasing an intensity level of at least one of the electrode stimulation signals to cause a change in pitch perception.

24. An audio prosthetic system according to claim 23, wherein the implantable electrode array is a cochlear implant array.

25. An audio prosthetic system according to claim 24, wherein the cochlear implant array is a deep insertion array.

26. An audio prosthetic system according to claim 23, wherein the implantable electrode array is a brainstem array.

27. An audio prosthetic system according to claim 23, wherein the set of electrode stimulation signals is a set of monopolar stimulation signals.

28. An audio prosthetic system according to claim 19, further comprising:
means for developing feedback information resulting from the stimulation of the audio nerve tissue.

29. An audio prosthetic system according to claim 28, wherein the feedback information includes subjective feedback information from an implanted patient user.

30. An audio prosthetic system according to claim 28, wherein the feedback information includes objective feedback information from an implanted device.

31. An audio prosthetic system according to claim 28, further comprising:
means for adjusting the system based on the feedback information to customize fit of the implantable electrode array for an implanted patient user.

32. An audio prosthetic system according to claim 23, wherein increasing the intensity level of the at least one of the electrode stimulation signals causes a perceived increase in pitch.

33. An audio prosthetic system according to claim 23, wherein increasing the intensity level of the at least one of the electrode stimulation signals causes a perceived decrease in pitch.

* * * * *